United States Patent [19]

Asano et al.

[11] Patent Number: 4,817,413

[45] Date of Patent: Apr. 4, 1989

[54] METHOD OF USING AN OPTO-ACOUSTIC APPARATUS FOR MEASURING CONCENTRATION OF GAS

[75] Inventors: Ichiro Asano; Toshihiko Uno, both of Minami, Japan

[73] Assignee: Horiba, Ltd., Kyoto, Japan

[21] Appl. No.: 838,564

[22] Filed: Mar. 11, 1986

Related U.S. Application Data

[62] Division of Ser. No. 567,802, Jan. 3, 1984, abandoned.

[30] Foreign Application Priority Data

Jan. 8, 1983 [JP] Japan .................................. 58-2614

[51] Int. Cl.⁴ ........................................... G01N 21/85
[52] U.S. Cl. ........................................... 73/24; 73/28
[58] Field of Search ..................... 73/24, 28; 250/343, 250/345; 356/434, 438, 439, 440; 310/25; 179/110 A

[56] References Cited

U.S. PATENT DOCUMENTS

| | | | |
|---|---|---|---|
| 3,513,415 | 5/1970 | Dostal | 310/25 |
| 3,546,500 | 12/1970 | Baumgartner | 310/25 |
| 3,559,100 | 1/1971 | Greb et al. | 310/25 |
| 3,998,557 | 12/1976 | Janaw | 356/434 |
| 4,163,382 | 8/1979 | Amer | 73/24 |
| 4,178,526 | 12/1979 | Nakamura et al. | 310/25 |
| 4,193,008 | 3/1980 | Naramura | 310/25 |
| 4,200,399 | 4/1980 | Kimble et al. | 73/24 |
| 4,255,964 | 3/1981 | Morison | 73/24 |
| 4,480,191 | 10/1984 | Karpowycz | 250/343 |
| 4,489,239 | 12/1984 | Grant et al. | 250/343 |
| 4,594,004 | 6/1986 | Ishida et al. | 73/24 |

FOREIGN PATENT DOCUMENTS

| | | | |
|---|---|---|---|
| 2089972 | 6/1982 | United Kingdom | 250/343 |
| 8200717 | 3/1982 | World Int. Prop. O. | 250/345 |

Primary Examiner—David L. Lacey
Attorney, Agent, or Firm—Wenderoth, Lind & Ponack

[57] ABSTRACT

A method of using an opto-acoustic apparatus for measuring, in an environment containing extraneous noise, the concentration of a gas in a mixture of gases or of particulates in a gas. The method is constituted by the steps of providing a measuring opto-acoustic cell having gas inlet and gas outlet for receiving and discharging a gas containing a particulate or a mixture of gases containing a gas the concentration of which is to be measured, directing laser rays from a laser ray generating device into the opto-acoustic cell, placing a chopper in the path of the laser rays between the device and the cell and operating the chopper for chopping the laser rays at a frequency corresponding to the resonant frequency of the cell, providing a narrow band microphone having a resonator with a narrow resonance frequency range including the resonant frequency of the cell and sufficiently narrow to exclude unwanted noise signals from the environment in which the cell is located, placing the microphone on the cell for detecting the sound signal generated by changes in the internal pressure of the cell, and determining from the sound signal the concentration of the gas in the mixture of gases or the concentration of the particulates in the gas.

6 Claims, 1 Drawing Sheet

METHOD OF USING AN OPTO-ACOUSTIC APPARATUS FOR MEASURING CONCENTRATION OF GAS

This application is a division of now abandoned application Ser. No. 567,802, filed Jan. 3, 1984, now abandoned.

BACKGROUND OF THE INVENTION

1. Field of the Invention

The present invention relates to an opto-acoustic apparatus and a method for using it for measuring the concentration of gas in a mixture of gases and the apparatus comprises providing an opto-acoustic cell into which a mixture of gases including the gas the concentration of which is to be measured is introduced, directing laser rays from a laser device for directing laser rays into said opto-acoustic cell, placing a chopper in the path of the laser rays for chopping the laser rays directed from said laser device, and placing a microphone in the cell for detecting the sound signal generated by the changes in the internal pressure in said opto-acoustic cell and determining the concentration of the gas from the sound signal.

2. Description of the Prior Art

There has heretofore been provided an apparatus for measuring the concentration of solid molecules in a gas introduced into an opto-acoustic cell, e.g., the concentration of particulates, such as smoke, in the exhaust gas of internal combustion engines and the like, and the concentration of specific gas molecules in a mixture of gases, e.g., the concentration of gas molecules such as ammonia, ethylene, and ozone in air, by utilizing an opto-acoustic effect.

An example will be described of the measurement of the concentration of particulates in the exhaust gas of an automobile engine. When laser rays are directed into the exhaust gas of such an engine, which exhaust gas has been introduced into an opto-acoustic cell and contain particulates therein, said particulates absorb optical energy and are heated. If said laser rays are chopped, said particulates are repeatedly heated and cooled in accordance with the chopping frequency, whereby a change of pressure, that is to say a change of acoustic pressure, is produced in said cell.

This change of acoustic pressure produces a sound wave, hereinafter referred to as a sound signal, which has a frequency equal to the chopping frequency of said laser rays. The strength of said sound signal is proportional to the amount of optical energy absorbed by said particulates. Thus, the concentration of said particulates can be measured by detecting said sound signal by means of a microphone and determining the strength thereof.

However, since said sound signal which is generated in said opto-acoustic cell is very weak, it has been necessary to use a highly sensitive microphone to detect said sound signal into a suitable electric signal, at present state it is necessary to use an expensive narrow band amplifier or a synchronizing rectifying amplifier, or both, for said amplifier means, since extraneous sounds, such as noise, may be large in comparison with said sound signal.

This is particularly true in the measurement of the concentration of particulates contained in the exhaust gas of an automobile engine. In such a case, exhaust noises are transmitted to said cell together with the exhaust gas. Accordingly, a muffler means such as buffer tank is installed in the exhaust feed passage. In addition, a muffler means such as buffer tank is also installed between said cell and a suction pump for preventing noise from being transmitted to said cell from said suction pump which draws gas into said cell.

It is, however, necessary to use an expensive large-scale muffler means in order to sufficiently reduce exhaust noises and suction noises. Besides, there are such defects that there is delay in the introduction of a sample, particulates tend to collect in said muffler means, and the like. These defects lead to errors in measurement, whereby there are natural limits to the effectiveness of said muffler means. Moreover, when there are noises more intense than the allowable range of said microphone and said amplifier, measurement becomes impossible.

SUMMARY OF THE INVENTION

The present invention seeks to provide a method of using an opto-acoustic apparatus which overcomes the drawbacks of the prior art as described above, and which is characterized by the provision of a narrow band microphone as the microphone for detecting the sound signal, and which microphone includes a resonator having a resonance frequency band including the chopping frequency of the laser rays and outside of which the other noises present in the engine, muffler, etc. lie.

In the use of the apparatus according to the present invention, it is only necessary to set the chopping frequency so that solid molecules and gas molecules, the concentration of which is to be measured, contained in the gas being analyzed will give sound signals within the resonance frequency band which can be detected by said microphone, so that the microphone will pick up sound signals only within the narrow frequency range in which the chopping frequency lies and which is outside the frequency range of exhaust noises and other noises. That is to say, the microphone selectively picks up the sound signals of the particles or gas being detected, and does not respond to noises in frequency ranges other than that of the sound signals, whereby highly accurate measurement of the concentration becomes possible merely by amplifying sound signals picked up which are uninfluenced by noise and other extraneous sounds. This is achieved without using the conventionally used highly sensitive microphone, an expensive large-scale narrow band amplifier and synchronizing rectifying amplifier, or a large-scale muffler means which is apt to result in troubles in the measurement. It goes without saying that the measurement of low concentrations can be achieved even if there are strong extraneous noises by simultaneously using a narrow band amplifier, a synchronizing rectifying amplifier, or a good muffler means even though it is simple.

BRIEF DESCRIPTION OF THE DRAWINGS

The invention will now be described in greater detail in connection with the accompanying drawings which show a preferred embodiment of the present invention. In the drawings.

DESCRIPTION OF THE PREFERRED EMBODIMENT

Figure 1:
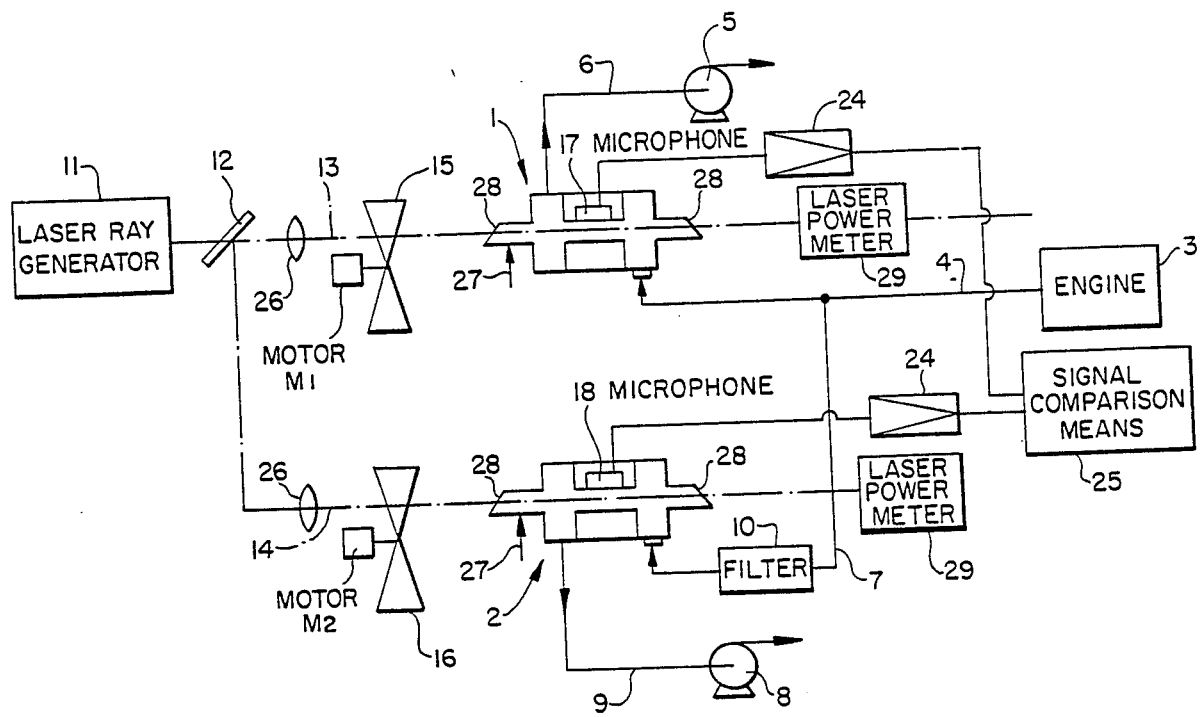
FIG. 1 is a block diagram of an opto-acoustic type apparatus used in the method according to the invention for measuring the concentration of a particulate in a gas or a gas in a mixture of gases.

Referring now to FIG. 1, there is diagrammatically shown an opto-acoustic apparatus used according to the method of the invention for measuring the concentration of particulates contained in exhaust gas, for example from an internal combustion engine. A measuring opto-acoustic cell 1 and a reference opto-acoustic cell 2 are positioned in parallel, and an introducing pipe 4 is connected for introducing the exhaust gas from an engine 3 into said measuring opto-acoustic cell 1. A gas exhausting pipe 6 provided with a suction pump 5 is connected with said measuring opto-acoustic cell 1. A branch pipe 7 branching from said introducing pipe 4 is connected to said reference opto-acoustic cell 2, and an exhaust pipe 9 provided with a suction pump 8 is connected with said reference opto-acoustic cell 2. Said branch pipe 7 has a filter 10 therein for removing particulates so that exhaust gas containing no particulates is introduced into said reference opto-acoustic cell 2.

A laser ray generating apparatus 11 is provided which generates laser rays. The rays from said laser apparatus 11 are directed to two optical paths 13 and 14 by means of a beam splitter 12. Said measuring opto-acoustic cell 1 is positioned on said optical path 13 while said reference opto-acoustic cell 2 is positioned on said optical path 14. Optical fibers can be used to direct the laser rays along the two paths, or alternatively two laser apparatuses can be used, one for each path.

A rotary chopper 15 for chopping laser rays is positioned in said optical path 13 and a rotary chopper 16 for chopping laser rays is positioned in said optical path 14. When chopped laser rays are directed into the gas introduced into said cells 1 and 2, as described above, sound signals having frequencies equal to the chopping frequencies of the laser rays are generated in said cells 1 and 2. Said chopping frequencies are chosen so that the frequencies of these sound signals are outside the range of frequencies of the exhaust sounds from said engine 3, the suction sounds of said pumps 5 and 8, and other extraneous noises in the system which way impinge on the cells.

Said chopping frequencies can be easily set and changed by, for example, separately rotating said choppers 15 and 16 by means of DC motors $M_1$ and $M_2$ and adjusting the DC voltage of said DC motors $M_1$ and $M_2$. The chopping frequency of the chopper 15 is preferably set to the resonance frequency of said cell 1 positioned in said optical path 13, while the chopping frequency of the chopper 16 is preferably set to the resonance frequency proper of said cell 2 positioned in said optical path 14. It goes without saying that the resonance frequencies of said cells 1 and 2 must be outside the ranges of the frequencies of the above described various kinds of noises.

Microphones 17 and 18 are provided, which are mounted on said cells for detecting sound signals generated in said cells. Said microphones 17 and 18 are positioned at the central portions of said cells where said sound signals are the strongest.

Figure 2:
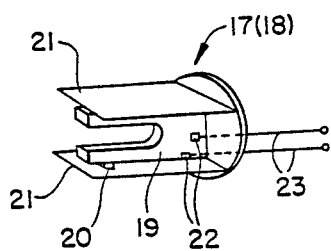
FIG. 2, FIG. 3 and FIG. 4 are perspective views showing embodiments of a microphone for use in the apparatus of FIG. 1.

Said microphones 17 and 18, as shown in FIG. 2, consist of a tuning fork type resonator 19 and vibrating plates 21 mounted on said resonator through connecting elements 20 at the place where said resonator 19 resonates most strongly. Said resonator 19 is preferably made of crystal which is a piezo-electric material resonating in the range of a narrow frequency band including the resonance frequencies of said cells and which generates piezo-electricity when vibrating resonantly. Said vibrating plates 21 are vibrated by said sound signals, and this vibration is transmitted to said resonator 19 through said connecting elements 20. When said sound signals are in the resonant frequency band of the resonator 19, it vibrates resonantly and puts out electric signals corresponding to the vibrations from an electrode 22 to a terminal 23. Said connecting elements 20 are made of a material which transmits vibration well.

An amplifier is connected to each of the microphones 17 and 18 and the amplifiers are connected to a conventional signal comparison means 25 for comparing the signals from the measuring cell and the reference cell. The output of said signal comparison means 25 is an indication of the concentration of the particulates in the gas. Condenser lenses 26 are provided between the laser ray generator and the choppers. Feeding pipes 27 for purge air are connected to the cells 17 and 18. Brewster's windows 28 are provided at each end of each cell, and a laser power meter 29 is provided at the opposite end of each cell from the laser ray generator.

In the above described apparatus, the influences of interfering ingredients contained in the exhaust gas can be eliminated, and the concentration of particulates can be measured from the electric signals picked up by the microphones. In addition, if the power of the laser rays varies, a correction of the output signals picked up by the microphones can be carried out on the basis of the laser ray power detected by said laser power meter 29.

Further, even if the measuring cell 1 and said reference cell 2 are of the same shape, but one or more of the pressure in said measuring cell 1, the density of the gas flowing through said measuring cell 1, and the specific heat of the gas flowing through said measuring cell 1 are different from the pressure in said reference cell 2, the density of the gas flowing through said reference cell 2, and the specific heat of the gas flowing through said reference cell 2, as a result of which the resonance frequency of said measuring cell 1 is different from the resonance frequency of said reference cell 2, the frequency of chopping of the laser rays can be easily adjusted so as to be made equal to the resonance frequencies of the respective cells 1 and 2 by adjusting the speed of rotation of said choppers 15 and 16. This will improve the accuracy of the measurement.

Figure 3:
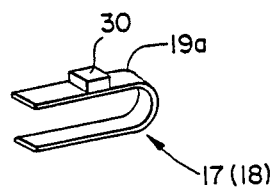
Figure 4:
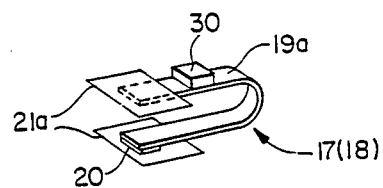

FIG. 3 shows another embodiment of the microphones 17 and 18. The microphone of this embodiment consists of a metallic tuning fork type resonator 19a having a narrow range of resonance frequencies including the resonance frequencies of the cells and a piezoelectric element 30 which produces an electric signal from the vibrations of said resonator 19a. To increase the sensitivity, vibrating plates 21a can be mounted on the arms of the resonator 19a through connecting members 20 as shown in FIG. 4.

What is claimed is:
1. A method of using an opto-acoustic apparatus for measuring, an environment containing extraneous noise, the concentration of a gas in a mixture of gases or of particulates in a gas, comprising:
   providing a measuring opto-acoustic cell having gas inlet and gas outlet means for receiving and discharging a gas containing particulates or a mixture of gases containing a gas the concentration of which is to be measured;

placing said cell in an environment containing extraneous or unwanted noise signals;

directing laser rays from a laser ray generating device into said opto-acoustic cell;

placing a chopper in the path of the laser rays between said device and said cell and operating said chopper for chopping the laser rays at a frequency corresponding to the resonant frequency of said cell;

providing a narrow band microphone having a resonator with a narrow resonance frequency range including the resonant frequency of said cell and sufficiently narrow to exclude the extraneous or unwanted noise signals from the environment in which said cell is located;

placing said microphone on said cell for detecting the sound signal generated by changes in the internal pressure of said cell; and determining from said sound signal the concentration of the gas in the mixture of gases or the concentration of the particulates in the gas.

2. A method as claimed in claim 1 further comprising placing a reference opto-acoustic cell in parallel with said measuring opto-acoustic cell and having gas inlet means and gas outlet means, and causing a reference gas free of the gas the concentration of which is to be measured or free of the particulates to flow through said reference opto-acoustic cell, said reference cell having a resonant frequency substantially the same as that of said measuring cell, directing corresponding laser rays into said reference opto-acoustic cell, placing a further microphone on said reference cell which is the same as the microphone on said measuring cell, determining the concentration by comparing the signals from said microphones.

3. A method as claimed in claim 2 in which the step of providing said microphone comprises providing a microphone resonator which is comprised of a tuning fork resonator.

4. A method as claimed in claim 3 in which the step of providing said microphone resonator comprises further providing a pair of vibrating plates, one on each arm of said tuning fork resonator, and connecting elements connecting said vibrating plates and said tuning fork resonator.

5. A method as claimed in claim 2 in which the step of providing said microphone resonator comprises providing a microphone resonator of piezo-electric crystal material.

6. A method as claimed in claim 2 in which the step of providing said microphone resonator comprises providing a metal material tuning fork resonator.

* * * * *